(12) United States Patent
Krehl

(10) Patent No.: US 7,648,531 B2
(45) Date of Patent: Jan. 19, 2010

(54) ENDOPROSTHESIS, IN PARTICULAR KNEE JOINT PROSTHESIS

(76) Inventor: Frieder W. Krehl, Villingen-Schwenningen (DE)

( * ) Notice: Subject to any disclaimer, the term of this patent is extended or adjusted under 35 U.S.C. 154(b) by 136 days.

(21) Appl. No.: 11/976,003

(22) Filed: Oct. 19, 2007

(65) Prior Publication Data

US 2008/0103607 A1 May 1, 2008

(30) Foreign Application Priority Data

Oct. 27, 2006 (DE) .................. 10 2006 051 393

(51) Int. Cl.
 *A61F 2/38* (2006.01)
 *A61F 2/32* (2006.01)
(52) U.S. Cl. .................. 623/20.32; 623/22.14
(58) Field of Classification Search ............... 623/18.11, 623/20.32–20.34, 22.13, 22.14
 See application file for complete search history.

(56) References Cited

U.S. PATENT DOCUMENTS 6,258,126 B1 * 7/2001 Colleran .................. 623/20.29

2005/0192674 A1 9/2005 Ferree .................. 623/23.41

FOREIGN PATENT DOCUMENTS

| EP | 1537839 A1 | 6/2005 |
|---|---|---|
| WO | WO 96/19162 | 6/1996 |
| WO | 99/42061 A1 | 8/1999 |
| WO | WO 2005/025451 A2 | 3/2005 |

* cited by examiner

*Primary Examiner*—Bruce E Snow
(74) *Attorney, Agent, or Firm*—The Nath Law Group; Jerald L. Meyer; Robert T. Burns

(57) ABSTRACT

The invention relates to an inlay which is suitable for an endoprosthesis, in particular a joint prosthesis. This inlay essentially comprises a flexible pad 5, a first flexible membrane 2 resting on the pad, and a second membrane 3, extending parallel to and above said membrane, in which support elements 5 are clipped. The support elements 4 rest with their undersides 4e on the first membrane 2, and with their surfaces 4a form a sliding and bearing surface for the joint head which is to be connected to the bone. The pad 5, composed of a liquid or gel-like medium, is situated in a well 1, and the two membranes 2 and 3 are fixed to the lateral walls 1a of the well by means of screws 6 and nuts 7.

9 Claims, 1 Drawing Sheet

ENDOPROSTHESIS, IN PARTICULAR KNEE JOINT PROSTHESIS

The invention relates to a joint prosthesis.

Such joint prostheses, referred to as artificial joints, are intended to replace a damaged or diseased joint, for example a knee joint.

In the case of the knee joint, joint prostheses are composed of metallic joint heads having an operative connection with the tibia and the femur. An inlay made of polyethylene, for example, is provided between the joint heads which prevents direct metal contact and partially compensates for the incongruence of the joint heads forming the upper and lower sections.

Because of the significant continuous strain which occurs essentially in places, the design of this inlay is problematic, resulting in cold flow, delamination, and abrasion of the inlay material.

An inlay has been proposed in the invention published in WO 99/42061, comprising a flexible pad, a flexible membrane resting on the pad, and support elements provided on the membrane whose surface is used for supporting the joint heads. Such an inlay reduces the frictional force and lessens the abrasion and introduction thereof into the tissue surrounding the joint, which can result in malfunction and damage.

For this design of the inlay, the connection of the support elements to the membrane is not detached. On the other hand, studies have shown that adhesive connections do not permanently withstand the shear forces which occur during the rolling motion of the joint heads.

The object of the present invention, therefore, is to provide a joint prosthesis having support heads which are permanently fixed without impairing the flexibility.

This object is achieved according to the present invention by means of a second membrane extending above and parallel to the first membrane, and having retaining openings in which the support elements are anchored and which laterally support one another and with their undersides rest on the first membrane, both membranes being attached to the base body.

The support elements rest on the first membrane and are connected to the adjacent support elements exclusively by means of the second membrane. The support element thus has limited mobility perpendicular to the membrane, the support elements resting laterally on the adjacent support elements. In an exemplary embodiment, the support elements located at the edges are able to rest on the lateral walls of the well, which acts as the base body and which absorbs the resulting shear forces so that the second membrane which is used for retaining the support element is not subjected to shearing.

Other exemplary embodiments illustrate a specialized design of the support elements.

Still other exemplary embodiments illustrate proposals for attaching the membrane to the base body, for selecting the material of the membranes and the support elements, and for the design of the pad.

Silicone in particular has proven to be a satisfactory material for the membrane due to its great flexibility.

An exemplary design according to yet another embodiment of the invention is particularly suited for knee joint prostheses.

The subject matter of the invention is explained in detail below with reference to one exemplary embodiment illustrated in the drawings, which show the following:

FIG. 1 illustrates an inlay designed according to the invention which normally is situated between the joint heads, generally made of steel, of the joint prosthesis, which in turn is joined by screws, pins, or with cement to the bone, and in the case of a knee joint prosthesis, is joined to the tibia or femur.

Figure 1:
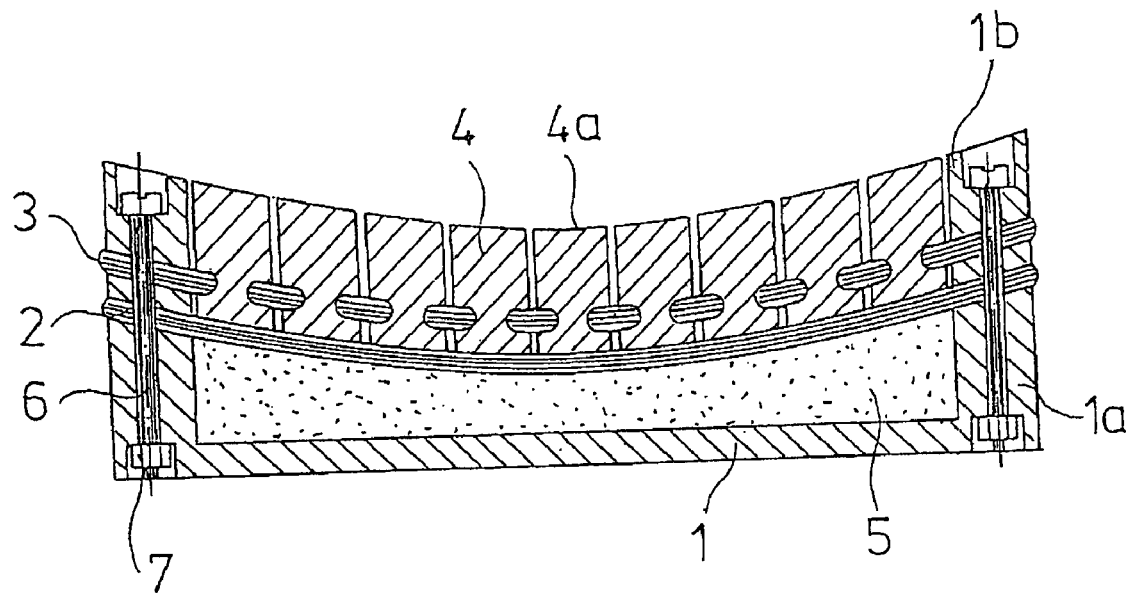
FIG. 1 shows a cross section of an inlay according to the invention for a knee joint prosthesis.

The inlay essentially comprises a flexible but noncompressible pad 5 on which a first membrane 2, and thereabove a second membrane 3 together with support elements 4 anchored therein, are situated. The membranes 2 and 3 are made of silicone, and the support elements 4 are made of polyethylene. The pad 5 is situated in a base body 1, designed as a well and likewise made of polyethylene, having lateral walls 1*a* extending to the surface 4*a* of the support elements 4. The membranes 2 and 3 are fixed to these walls 1*a* by means of screws 6 and nuts 7.

The surfaces 4*a* of the support elements 4 and 1*b* of the walls 1*a* of the well form a slightly concave bearing surface for the joint head (not illustrated), which has a convex surface.

Figure 3:
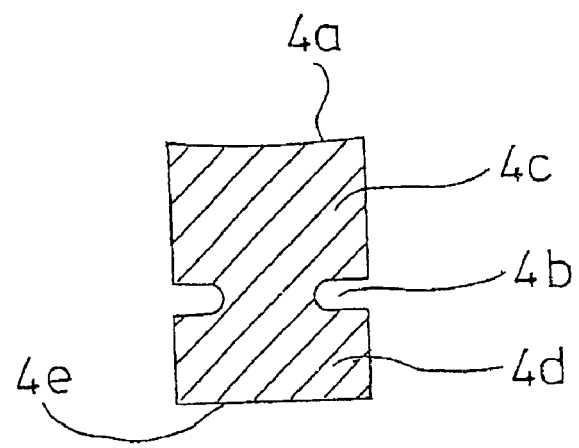
FIG. 3 shows an enlarged cross section of a support element.

As shown most clearly in FIG. 3, the support elements 4 which have a double T-shaped cross section are divided by a constriction 4*b* into an upper part 4*c* and a base part 4*d*. At their base part 4*d* the support elements are clipped and thus fixed in corresponding retaining openings in the membrane 2. The underside 4*e* of the base part is supported on the top side of the membrane 2. The support elements are adjacently aligned, with the outer support elements 4 being supported by the lateral walls 1*a* of the well 1.

Figure 2:
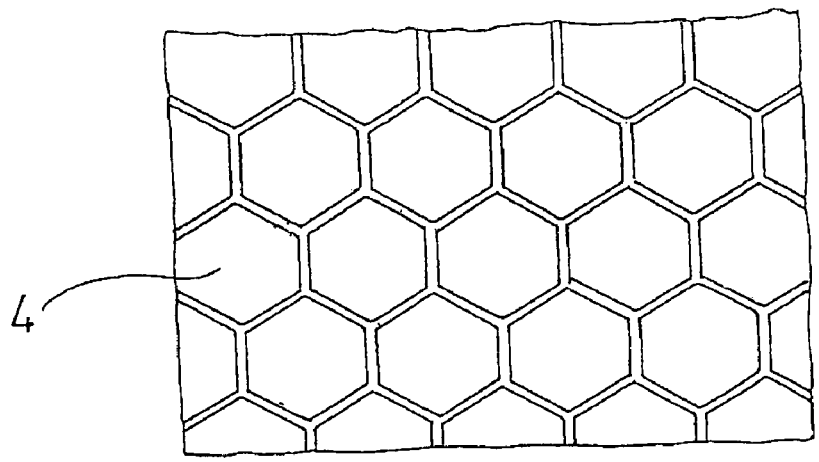
FIG. 2 shows an enlarged partial top view of the inlay according to FIG. 1.

As shown in the top view according to FIG. 2, the support elements have a hexagonal cross section, thus resulting in good support on all sides.

As a result of the measure according to the invention, the support elements 4 are supported in the transverse direction so that the membrane used for retaining the support elements is not subjected to shearing during movement of the joint.

The axially acting pressure forces are absorbed by the pad 5, which is composed of a fluid with little or no compressibility, preferably a saline solution or gel-like substance, provided in the well 1 and delimited from above by the membrane 2. This pad 5 provides uniform distribution of the hydrostatic pressure.

LIST OF REFERENCE NUMERALS

1 Base body, well
2 First membrane
3 Second membrane
4 Support element
   4*a* Support element surface
   4*b* Constriction
   4*c* Upper part
   4*d* Base part
   4*e* Support element underside
5 Pad
6 Screw
7 Nut

The invention claimed is:

1. Joint prosthesis having joint heads, between which an inlay is situated which comprises a flexible pad, a flexible first membrane resting on the pad, and support elements provided on the membrane whose surface is used for supporting one of the two joint heads, the pad and membrane being accommodated by a base body, characterized in that above the membrane (2) and extending parallel thereto a second membrane (3) is provided which has retaining openings, the support elements (4) are anchored in the second membrane (3) and laterally support one another and with their undersides (4e) rest on the first membrane (2), and both membranes (2 and 3) are attached to the base body (1).

2. Joint prosthesis according to claim 1, characterized in that by means of constrictions (4b) running parallel to the membranes (2 and 3) the support elements (4) are divided into an upper part (4c) and a base part (4d), and at their constrictions (4b) are fixed in the retaining openings in the second membrane (3).

3. Joint prosthesis according to claim 2, characterized in that the support elements (4) have a double T-shaped longitudinal section.

4. Joint prosthesis according to claim 1, characterized in that the support elements (4) have a hexagonal cross section.

5. Joint prosthesis according to claim 1, characterized in that the base body is designed as a well (1), the lateral walls (1a) of which extend to the surface (4a) of the support elements and laterally support the outer support elements (4).

6. Joint prosthesis according to claim 1, characterized in that the membranes (2, 3) are fixedly connected to the base body (1), preferably by means of screws (6, 7) which pass through the walls (1a) of the base body (1).

7. Joint prosthesis according to claim 1, characterized in that the membranes (2, 3) are made of silicone and the support elements (4) and the well (1) are made of polyethylene.

8. Joint prosthesis according to claim 1, characterized in that the well (1) for accommodating the pad (5) is filled with a saline solution or a gel-like substance, and is sealed by the first flexible membrane (2) on the load-bearing side.

9. Joint prosthesis according to claim 1, characterized by use as a knee joint prosthesis, in which the joint heads thereof may be joined to the tibia or femur.

* * * * *